(12) United States Patent
Valdastri et al.

(10) Patent No.: US 11,298,034 B2
(45) Date of Patent: Apr. 12, 2022

(54) WEARABLE TONOMETER

(71) Applicant: WIRELESS INTEGRATED NETWORK S.R.L., Cascina (IT)

(72) Inventors: Pietro Valdastri, Leghorn (IT); Ferdinando De Negri, Pisa (IT)

(73) Assignee: AB MEDICA S.P.A., Milan (IT)

( * ) Notice: Subject to any disclaimer, the term of this patent is extended or adjusted under 35 U.S.C. 154(b) by 671 days.

(21) Appl. No.: 16/090,616

(22) PCT Filed: Apr. 4, 2017

(86) PCT No.: PCT/IB2017/051904
§ 371 (c)(1),
(2) Date: Oct. 2, 2018

(87) PCT Pub. No.: WO2017/175120
PCT Pub. Date: Oct. 12, 2017

(65) Prior Publication Data
US 2019/0110701 A1  Apr. 18, 2019

(30) Foreign Application Priority Data

Apr. 4, 2016   (IT) .................. 102016000034368

(51) Int. Cl.
*A61B 5/022*    (2006.01)
*A61B 5/00*     (2006.01)
(Continued)

(52) U.S. Cl.
CPC .......... *A61B 5/02225* (2013.01); *A61B 5/022* (2013.01); *A61B 5/02108* (2013.01);
(Continued)

(58) Field of Classification Search
CPC . A61B 5/02225; A61B 5/318; A61B 5/02108; A61B 5/02125; A61B 5/022;
(Continued)

(56) References Cited

U.S. PATENT DOCUMENTS 5,179,956 A    1/1993 Harada et al.
6,491,647 B1   12/2002 Bridger et al.
(Continued)

FOREIGN PATENT DOCUMENTS

IL       166200 A       11/2010
WO       96/11625 A1    4/1996
WO    2013/068955 A1    5/2013

OTHER PUBLICATIONS

International Search Report, dated Sep. 25, 2017, corresponding to Application No. PCT/IB2017/051904.
(Continued)

*Primary Examiner* — Daniel L Cerioni
*Assistant Examiner* — Deirdre M Willgohs
(74) *Attorney, Agent, or Firm* — Ladas & Parry LLP; Malcolm J. MacDonald

(57) ABSTRACT

A tonometer for continuously monitoring arterial blood pressure of a patient, including a bracelet, a detection group mounted on the bracelet and arranged to detect a pressure signal. The detection group has a plurality of pressure sensors arranged to detect a pressure signal associated with the blood pressure wave of the patient. A pressure sensor is positioned in proximity of the radial artery of the patient, at the opposite side of the radial bone. A touching group is interposed between the detection group and the radial artery, and equipped with a plurality of protuberant members, each of which is associated with a pressure sensor, and arranged to be positioned into contact with the skin of the patient, in such a way to exert a predetermined force on the radial artery.

16 Claims, 10 Drawing Sheets

(51) Int. Cl.
*A61B 5/021* (2006.01)
*A61B 5/318* (2021.01)

(52) U.S. Cl.
CPC ...... *A61B 5/02125* (2013.01); *A61B 5/02233* (2013.01); *A61B 5/318* (2021.01); *A61B 5/681* (2013.01); *A61B 5/6843* (2013.01); *A61B 5/7203* (2013.01); *A61B 5/021* (2013.01); *A61B 5/6831* (2013.01); *A61B 5/6844* (2013.01); *A61B 2562/0247* (2013.01); *A61B 2562/04* (2013.01); *A61B 2562/043* (2013.01); *A61B 2562/046* (2013.01); *A61B 2562/14* (2013.01)

(58) Field of Classification Search
CPC ... A61B 5/02233; A61B 5/681; A61B 5/6843; A61B 5/7203; A61B 5/021; A61B 5/6831; A61B 5/6844; A61B 2562/0247; A61B 2562/04; A61B 2562/043; A61B 2562/046; A61B 2562/14; A44C 5/00; A44C 5/0007; A44C 5/0015; A44C 5/0023; A44C 5/003; A44C 5/0038; A44C 5/0046; A44C 5/0053; A44C 5/0061; A44C 5/0069; A44C 5/0076; A44C 5/0084; A44C 5/0092; A44C 5/14; A44C 5/142; A44C 5/145; A44C 5/147; A44C 5/16; A44C 5/18; A44C 5/185; A44C 5/20; A44C 5/2004; A44C 5/2009; A44C 5/2014; A44C 5/2019; A44C 5/2023; A44C 5/2028; A44C 5/2033; A44C 5/2038; A44C 5/2042; A44C 5/2047; A44C 5/2052; A44C 5/2057; A44C 5/2061; A44C 5/2066; A44C 5/2071; A44C 5/2076; A44C 5/208; A44C 5/2085; Y10T 24/2102; Y10T 24/2104; Y10T 24/2113; Y10T 24/2117; Y10T 24/2123; Y10T 24/2128; Y10T 24/2179; Y10T 24/2185; Y10T 24/2192; Y10T 24/47; Y10T 24/4736; Y10T 24/4745; Y10T 24/4782; Y10T 24/407
USPC ........................................................ 600/485
See application file for complete search history.

(56) References Cited

U.S. PATENT DOCUMENTS

| | | |
|---|---|---|
| 2009/0069698 A1 | 3/2009 | Bae et al. |
| 2010/0228311 A1 | 9/2010 | Naqvi et al. |
| 2013/0144176 A1 | 6/2013 | Lee |
| 2015/0289608 A1* | 10/2015 | Rivera ............... A44C 5/14 368/282 |

OTHER PUBLICATIONS

Edward J. Ciaccio, et al., "Tonometric Arterial Pulse Sensor With Noise Cancellation", IEE Transactions on Biomedical Engineering, vol. 55, No. 10, Oct. 2008, pp. 2388-2396.

* cited by examiner

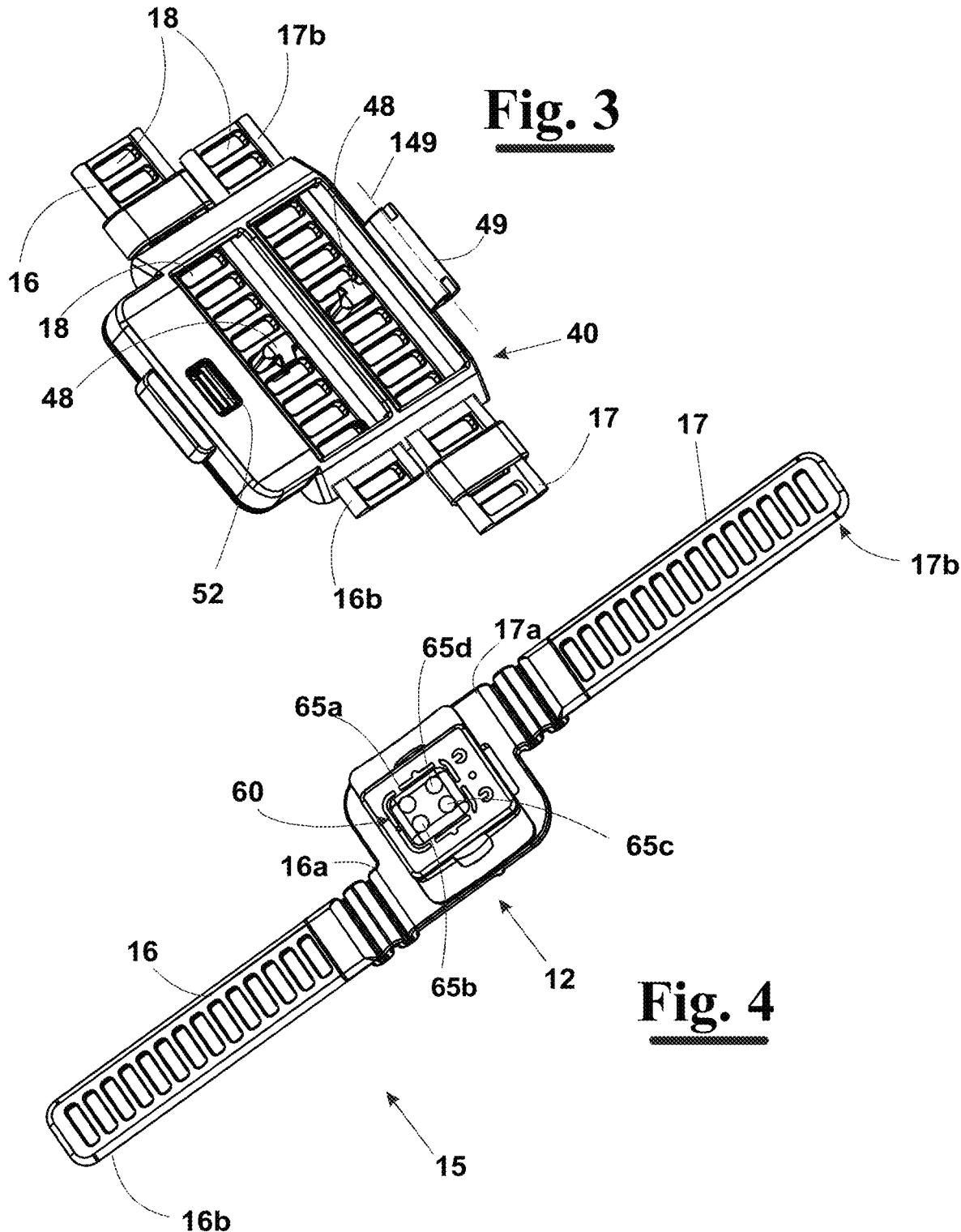

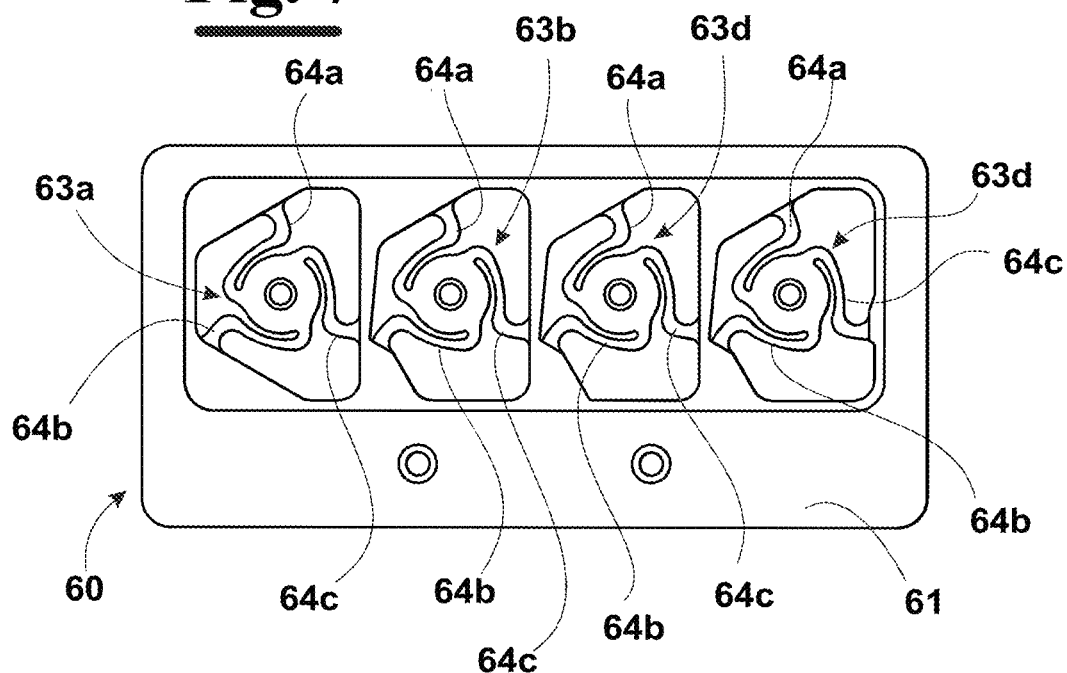
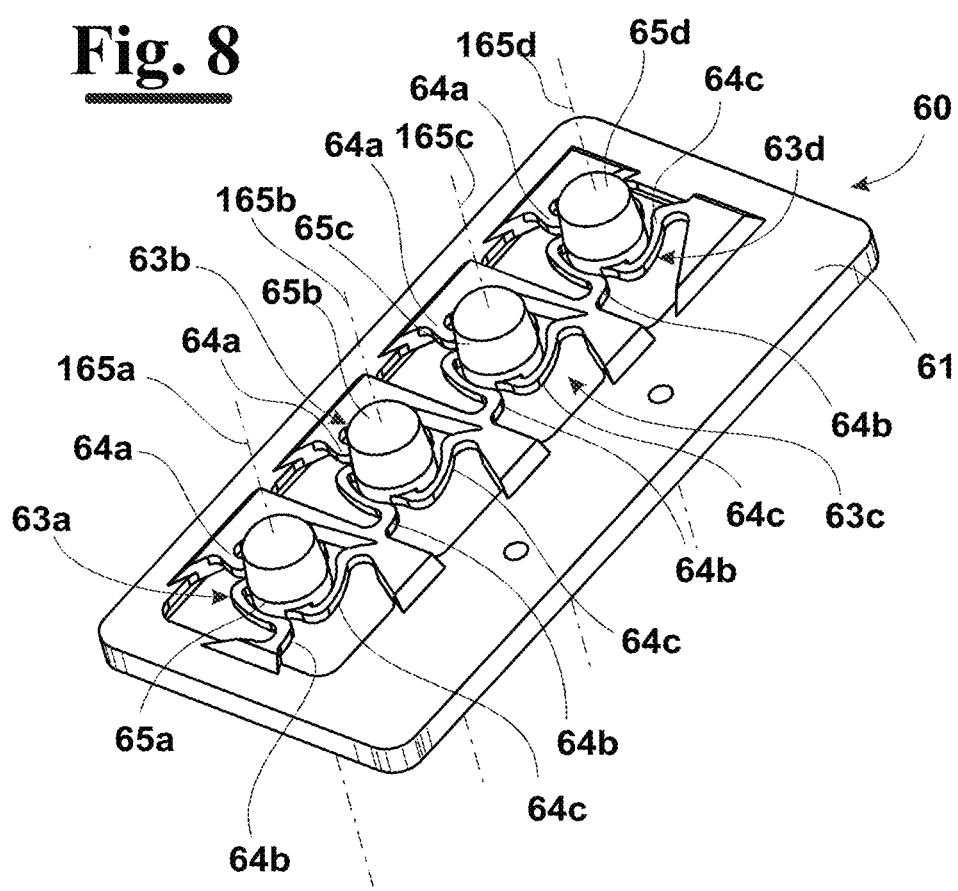

WEARABLE TONOMETER

FIELD OF THE INVENTION

The present invention relates to the medical field, and, in particular, it relates to a tonometer that is worn by a patient, for continuously and non-invasive monitoring of a superficial artery of a patient, as, for example, the radial artery.

Furthermore, the invention relates to a method for measuring that is carried out by the above mentioned tonometer.

DESCRIPTION OF THE PRIOR ART

As known, the arterial blood pressure is one of the more useful parameters for diagnosing cardiovascular diseases, and for obtaining a follow-up in patients suffering from these diseases.

The tonometer is a non-invasive apparatus that allows to detect the arterial blood pressure, by compressing a superficial artery, for example the radial artery, against the bone structures arranged below it. From the arterial blood pressure are, then, determined, by using an appropriate algorithm, both the central arterial blood pressure, and the central aortic pressure, both systolic and diastolic.

A wearable clock-shaped tonometer is disclosed in IL166200. The use of a clock-shaped tonometer allows, on the one hand, to make the tonometer comfortable to be wound, and on the other hand, to motorize the arterial blood pressure in a patient also for a long period of time even far away from a specialized centre, and without the support of a qualified person. In particular, the device of IL166200 comprises a pressure sensor that is immersed in a chamber containing a transmission fluid, for example a gel. The chamber is arranged into contact with the artery and the transmission fluid transmits forces that arise from the deformation of the artery. Opposite to the sensor chamber, a display unit is provided by which the data measured by the sensor can be displayed.

However, this solution provides to use a single pressure sensor, and, therefore, when the device is wound by the patient, it moves away from the starting position, and the artery signal is inevitable lost.

In order to overcome this drawback, devices have been developed that provide an array of sensors. For example, a tonometer of this type is described in US2009069698. In this case, a control unit is provided that, according to the intensity and to the quality of the signals received from each sensor, selects the sensor with the best signal, and carries out the measurement through the sensor so identified. In this way, the reliability of the tonometer is increased with respect to the previous case, because the pressure sensor is selected that is the one best positioned above the artery.

However, during the measurement of the pressure signal, the device described in US2009069698 is affected by background errors due, in particular, to the cross talk between the different sensors.

Furthermore, due to the movement of the wrist, or due to a push, the tonometer can move from a starting position, whereby the sensor that has been initially selected, can lose the signal becoming a sensor that is not able to correctly detect the blood pressure wave of the patient.

In Edward J. Ciaccio and Gary M. Drzewiecki "Tonometric arterial pulse sensor with noise cancellation" IEEE Transactions on Biomedical Engineering, vol. 55, no. 10, October 2008, a device is described for permanently non-invasively monitoring the pressure wave of an artery. In particular, two piezoelectric sensors are provided in order to eliminate artifacts that reduce the quality of the signal, in particular movement artifacts and background noise. A first sensor is located at the radial artery (p) and another sensor is positioned in such a way that to prevent any overlapping with the artery pulsation (n). A step of noise removal is conventionally carried out using a reference input, or reducing the movement and noise artifacts from the acquired artery pulsation tonometric signal.

Even in this case, the arrangement of the sensor upon the artery must be carried out with precision, so that the received measurement signal is strong enough.

A further tonometric device of known type provides a detection unit comprising a determined number of sensors immersed in a gel and an interface positioned into contact with the skin and made of plastic and rubber. However, these materials generate a nonlinearity in the transmission of the applied force/pressure, thus deforming the plethysmographic curve and, therefore, possible measurement errors.

In WO2013/068955 in the name of the same Applicant, a tonometer is described comprising a support body that can be wound by a patient and a detection unit mounted on it, and comprising a determined number of sensors. Between the sensors and the wrist of the patient an element made of silicone rubber is provided.

Another example of wearable tonometer, analogous to the previous, is described in U.S. Pat. No. 6,491,647. In this case, linear springs are provided elastically supporting the touching member that is arranged, in use, into contact with the skin of the patient.

Notwithstanding, both these solutions of prior art have some drawbacks. In fact, both the silicone rubber of WO2013/068955, and the linear springs of U.S. Pat. No. 6,491,647 are not capable to transmit the pressure pulses without modifying the signal. In other words, the shape of the pressure signal that is detected by the sensors has, in both the cases, a high level of noise and, therefore, these solutions do not allow to accurately measure the arterial blood pressure.

SUMMARY OF THE INVENTION

It is, therefore, an object of the invention to provide a wearable tonometer that allows to improve the sensibility of the sensors, in particular increasing the ratio between the detected signal and the noise, in particular due to the cross talk between the different sensors that are used.

It is also an object of the invention to provide a wearable tonometer that is able to guarantee that the force applied on the wrist of the patient, that is necessary for measuring the blood pressure wave, is constant.

It is another object of the invention to provide a wearable tonometer that is able to guarantee that the same is maintained in a correct position on the wrist of the patient for all the measurement time in such a way to obtain an accurate and reliable measurement signal.

These and other objects are achieved by an improved tonometer for continuously monitoring the arterial blood pressure of a patient for a predetermined period of time, said tonometer comprising:
- a bracelet configured in such a way to be applied to a wrist of a patient;
- a detection group mounted on the bracelet and configured for detecting a pressure signal, said detection group comprising a plurality of pressure sensors arranged to detect a respective pressure signal associated to the blood pressure wave of the patient, at least a pressure sensor of said plurality being positioned, in use, in proximity of the radial artery of the patient, at the opposite side of the radial bone;

a touching group interposed, in use, between the detection group and the radial artery of the patient, said touching group equipped with a plurality of protuberant members, each protuberant member of said plurality arranged to be positioned, in use, into contact with the skin of the patient, in such a way to exert a predetermined force F su said radial artery and to transmit the received pressure pulses to a respective pressure sensor associated to it;

a processing unit arranged to process the pressure signal detected dal detection group in such a way to determine the blood pressure wave of the patient;

whose main characteristic is that the touching group is made of a material having a predetermined elastic constant greater than the elastic constant of the radial artery, that the touching group comprises a base portion that is integral, in use, to the detection group and a plurality of connection portions, each of which arranged to elastically connect a respective protuberant member to the base portion, and that each connection portion comprises a plurality of connection arms configured in such a way to have a controlled elastic flexibility along a predetermined direction substantially orthogonal a said base portion, such that each protuberant member is able to elastically move along a direction that is substantially orthogonal to the base portion.

In particular, the technical solution according to the present invention allows to have an elastic response, because, with respect to the prior art solutions, the ration between the elastic contribution and the viscous contribution, is increased. In this way, it is possible to reduce the cross talk between the sensors, and, therefore, to increase their sensibility.

Other features of the present invention are described in the dependent claims.

In a first embodiment, both the connection portion and the base portion, and the protuberant members are made of a plastic material having an elastic constant greater than the elastic constant of the radial artery.

Advantageously, the plastic material can be a thermoplastic material, e.g. Acrylonitrile Butadiene Styrene, or ABS. In this way, it is possible to simplify and reduce the costs related to the production process.

In particular, the whole touching group can be produced by moulding of plastic material.

In an alternative embodiment, the connection portion is made of a metallic material, whereas, the base portion and the protuberant members are made of a plastic material having an elastic constant greater than the elastic constant of the radial artery.

In particular, it is, furthermore, provided an adjusting device arranged to bring/move away the touching group near to/from said radial artery, in such a way to adjust the force F that is exerted by the touching group on the wall of the radial artery.

Advantageously, the adjusting device comprises a worm screw on which the touching group is slidingly mounted along a direction that is substantially orthogonal to the wrist of the patient. In particular, an operating knob can be provided, acting on which the sliding of the touching group along the worm screw is operated.

In a possible embodiment, the detection group comprises at least 3 pressure sensors positioned in a row. Therefore, in this case, the touching group comprises, in its turn, at least 3 respective protuberant members, also these positioned in a row. However, other alternative embodiments are provided comprising, in particular, a different number of sensors positioned along a single row, or positioned according to an array comprising a predetermined number of rows and a predetermined number of columns.

In particular, the bracelet can comprise:
a support portion arranged to engage, in use, said detection group;
a strap made of a flexible material and comprising a first portion and a second portion having a respective first end fixed to the support portion, at opposite sides, and a respective second end, which is free;
an engagement device arranged to engage, in use, said first and said second portion of said strap.

Advantageously, a locking device is, furthermore, provided that is arranged to maintain in a locking configuration the engagement device and the containing body. In this locking configuration, the first and the second portion of the strap are tightened between the engagement device and the containing body.

Advantageously, the engagement device provides a main body having a first and a second aperture positioned at opposite sides and arranged to tighten, in use, the second end of the first portion and the second end of the second portion of the strap, respectively.

According to another aspect of the invention, an improved tonometer for continuously monitoring the arterial blood pressure of a patient for a predetermined period of time comprises:
a bracelet configured in such a way to be applied to a wrist of a patient;
a detection group mounted on the bracelet and arranged to detect a pressure signal, said detection group comprising a plurality of pressure sensors arranged to detect a respective pressure signal associated to the blood pressure wave of the patient, at least a pressure sensor of said plurality being positioned, in use, in proximity of the radial artery of the patient, at the opposite side of the radial bone;
a processing unit arranged to process said pressure signal detected da said detection group in such a way to determine the blood pressure wave of the patient;
a containing body arranged to house, in use, said processing unit;
and wherein the bracelet comprises:
a support portion arranged, in use, to engage said detection group;
a strap made of a flexible material and comprising a first portion and a second portion having a respective first end fixed to the support portion at opposite sides, and a respective second end, which is free;
an engagement device arranged to engage, in use, said first and said second portion del strap;
a locking device arranged to maintain in a locking configuration said engagement device and said containing body, in said locking configuration said first and said second portion of said strap being tightened between said engagement device and said containing body, in such a way to lock said bracelet in a correct position with respect to the arm of the patient, in which said detection group is positioned at the artery of the patient and said containing body is positioned at the upper substantially flat of the wrist of the patient.

In particular, the engagement device is positioned, in use, at the opposite side of the support portion with respect to the wrist of the patient.

According to a further aspect of the invention, a system for determining the arterial blood pressure of a patient comprises:
- a tonometer as above described arranged to generate a tonometric curve;
- an ECG device arranged to generate an electrocardiographic curve;
- a microcontroller arranged to process the electrocardiographic curve and the tonometric curve of the patient undergoing examination at determined instants (ti) for determining the pulse transit time, or PTT, i.e. the delay between the 2 curves, in particular by computing the delay between a r-peak of the electrocardiographic curve and a corresponding peak of the tonometric curve, said microcontroller, then, arranged to associate said computed delay to a determined reference value of the arterial blood pressure and a measure a said determined instants (ti), the difference ΔPA(ti) between the value PA1(ti) of the arterial blood pressure of the patient, estimated by the pulse transit time, and the value PA2(ti) of the arterial blood pressure estimated by the tonometric curve.

In particular, if the above difference between PA1(ti) and PA2(ti) is greater than a predetermined threshold value, the microcontroller operates an oscillometric device arranged to measure an arterial blood pressure value PA3(ti) by oscillometric technique.

Then, the microcontroller is arranged to associate said arterial blood pressure value PA3(ti) both to the value PA2(ti) of the arterial blood pressure estimated by the tonometric curve, and to the value PA1(ti) of arterial blood pressure estimated by the pulse transit time. In other words, the microcontroller is arranged to start a calibration step in which the value of the arterial blood pressure estimated by the sole tonometric curve PA2(ti) and the one estimated by the delay between the tonometric curve and electrocardiographic curve PA1(ti) are aligned with the one estimated with the oscillometric technique PA3(ti).

More precisely, the oscillometric device is arranged to determine the arterial blood pressure of the patient by processing the air oscillations registered inside a muff that is applied to an arm of the patient, during the deflating step. When the microcontroller detects a difference exceeding a predetermined threshold value PA*(ti) between the arterial blood pressure value measured by the tonometer PA1(ti), and the value of the arterial blood pressure estimated by the technique of pulse transit time PA2(ti), it operates the oscillometric device in such a way to obtain a value of the arterial blood pressure of calibration PAC(ti). The microcontroller proceeds, then, to associate this value of the arterial blood pressure of calibration both to the value of the arterial blood pressure determined by the tonometer and the value of the arterial blood pressure determined by the pulse transit time.

BRIEF DESCRIPTION OF THE DRAWINGS

The invention will now be shown with the following description of its exemplary embodiments, exemplifying but not limitative, with reference to the attached drawings in which:

FIGS. 3 and 4 show, in perspective views, some details of the strap, and the relative locking device, of the tonometer, according to the invention;

FIGS. 7 and 8 show in a plan view and in a perspective view, respectively, a first embodiment of a touching group according to the invention;

DETAILED DESCRIPTION OF THE INVENTION

Figure 1:
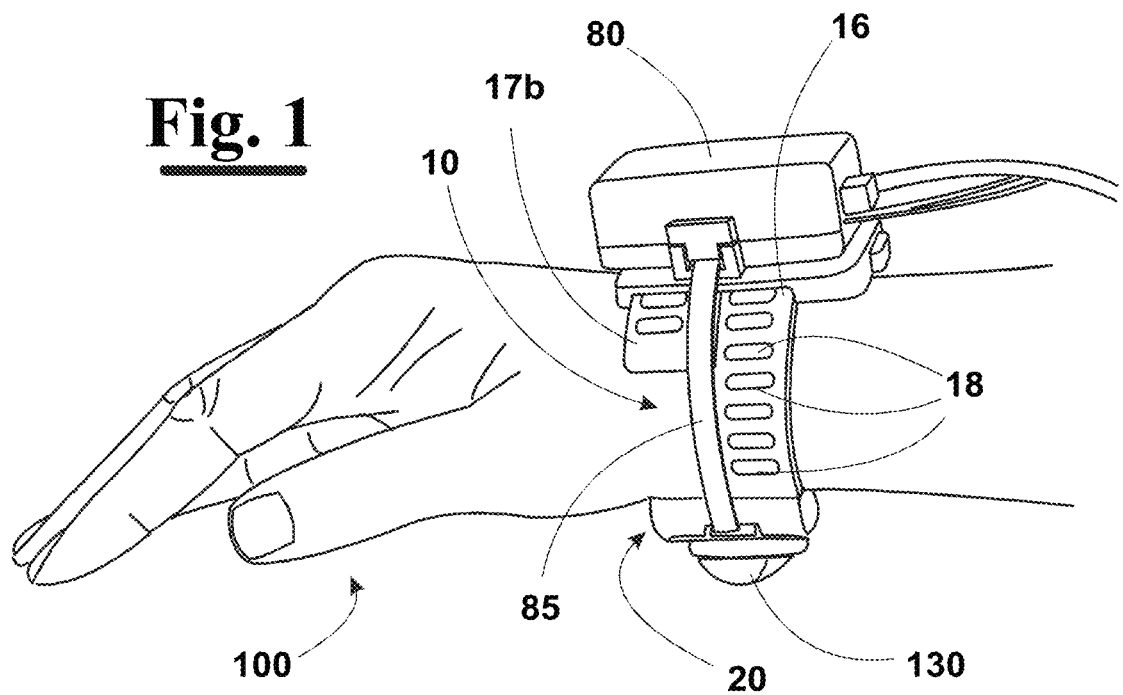
FIG. 1 is a perspective view of the tonometer, according to the invention, applied to a wrist of a patient.
Figure 2:
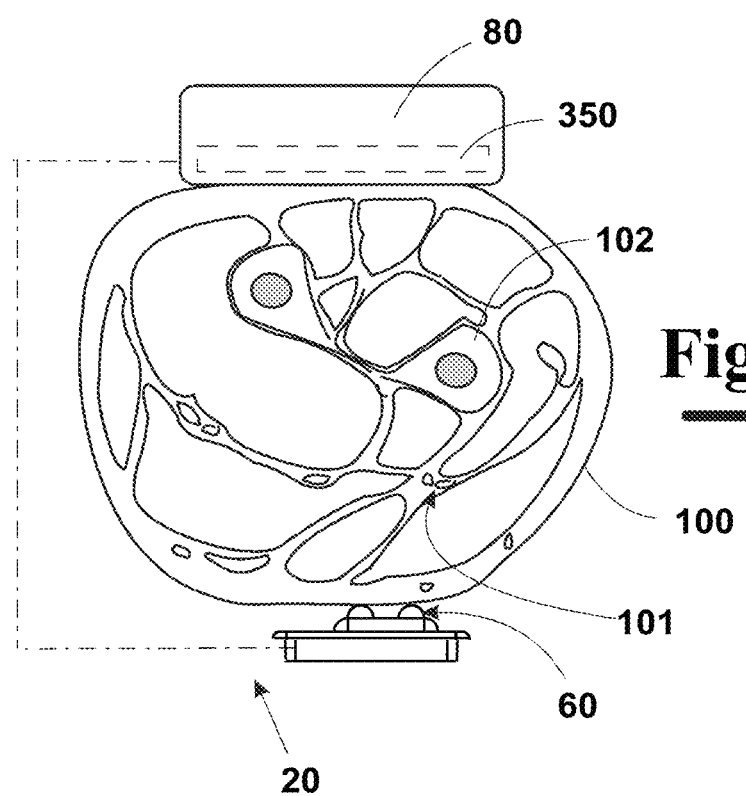
FIG. 2 diagrammatically shows, in a sectioned view, the working position of the tonometer of FIG. 1 with respect to the artery and the radial bone of the patient.

With reference to FIG. 1, an improved tonometer 1 for continuously monitoring the arterial blood pressure of a patient for a predetermined period of time, comprises a bracelet 10 configured in such a way to be applied to a wrist of the patient 100. The tonometer 1 provides, furthermore, a detection group 20 mounted on the bracelet 10 and arranged, in operating conditions, to detect a pressure signal. As diagrammatically shown in the FIGS. 11 and 12, the detection group 20 comprises at least 2 pressure sensors 25, for example of piezoresistive, or piezoelectric type, arranged to detect a respective pressure signal associated to the blood pressure wave of the patient 100. More precisely, at least a pressure sensor 25 of the detection group is positioned, in use, in proximity of the radial artery of the patient 100, at the opposite side of the radial bone. More in detail, the sensors 25 are arranged to provide a pressure signal when the detection group 20 detects the differences of pressures in the artery 101 of the patient 100. This event happens, as will be described in detail below, when artery 101 is subjected to a determined force F that is able of causing a determined flattening level of the same.

The tonometer 1 provides, furthermore, a touching group 60 interposed, in use, between the sensors 25 and the radial artery 101 of the patient. More in detail, the touching group 60 is equipped with a plurality of protuberant members, e.g. 4 protuberant members 65a-65d, each of which associated to a respective pressure sensor 25. The protuberant members 65a-65d are arranged to be positioned, in use, into contact with the skin of the patient, in such a way to exert a predetermined force F on the radial artery. It is, then, provided a processing unit 350 arranged to process the pressure signal detected by the detection group 20 and with which is connected by means of a wire connection 85 (see FIG. 1), or, alternatively, by means of a wireless connection, in such a way to determine the blood pressure wave of the patient. The processing unit 350 can be housed, for example, within a containing body 80.

According to the invention, the touching group 60 is made of a stiff material, and comprises a base portion 61 that is integral, in use, to the detection group 20 and a predetermined number of connection portions, for example 4 connection portions 63a-63d. Each connection portion 63a-63d is arranged, in particular, to elastically connect a respective protuberant member 65a-65d to the base portion 61. More precisely, each connection portion 63a-63d is configured such that the respective protuberant member 65a-65d is able to elastically move along a direction 165a-165d substantially orthogonal to the base portion 61, in particular to the plane on which it lays. More in particular, each connection portion 63a-63d comprises a plurality of connection arms, for example 3 connection arms 64a,64b,64c configured in such a way to have a controlled elastic flexibility along said predetermined direction 165a-165d substantially orthogonal to the base portion 61.

In particular, with respect to other solutions of prior art, in particular to the solution described in WO2013/068955 in the name of the same Applicant, where between the detection group and the wrist of the patient an element made of silicone rubber is provided, the present invention allows to obtain an improved signal, greatly reducing the noise. In fact, the silicone rubber, as well as other materials that are used in the prior art, even though they have mainly an elastic behaviour, however, they always have also a viscoelastic component. This modifies the shape of the pressure signal detected by the sensors and, therefore, does not allow to accurately measure the blood pressure wave.

Therefore, the solution according to the invention, allows to considerably improve the accuracy of the signal "amplifying" the same, and reducing the noise, in particular, due to the cross-talk, between the different sensors.

As known, in fact, a limit of the pressure sensors that are normally used for measuring the blood pressure is to be highly flexible. In particular, these sensors are much more flexible than the artery, therefore, the detected pressure is affected by the flexibility of the artery same. In order to overcome this drawback, the present invention provides to use materials having a high elastic constant, more precisely an elastic constant higher than the one of the artery. However, it is also necessary that the elastic constant at the engagement portions 63a-63d is comparable to that of the artery, in such a way that they can deform according to the pressure signal. This is achieved by the present invention due to the particular geometry of the connection portions 63a-63d that allows to locally reduce the stiffness of the structure and, therefore, to each protuberant member 65a-65d, to move in a controlled way along a predetermined direction. In this way, the detection by the sensors of the blood pressure wave is optimized up to be highly accurate.

In the FIGS. 7 to 10 each protuberant member 65a-65d is associated to 3 shaped connection arms 64a-64c, however each protuberant member 65a-65d can be associated to a different number of arms, for example 4, or 5, or 6. In particular, the connection arms 64a-64c work in flexion and/or in torsion. More in particular, each connection arm 64a-64c is a shaped arm, for example substantially S-shaped, and is arranged to lay, in a rest position, on a plane that is substantially orthogonal to the movement direction 165a-165d of the protuberant members 65a-65d.

Advantageously, the connection arms 64a-64c of a same connection portion 63a-63d are symmetrically arranged about the direction 165a-165d that is substantially orthogonal to the base portion 61 and, therefore, with respect to the protuberant member 65a-65d.

In a possible embodiment of the invention, each connection portion 63a-63d is made of a metallic material, whereas, both the base portion 61 and the protuberant members 65a-65d are made of a stiff plastic material, in particular having an elastic constant greater than the elastic constant of the radial artery.

Figure 9:
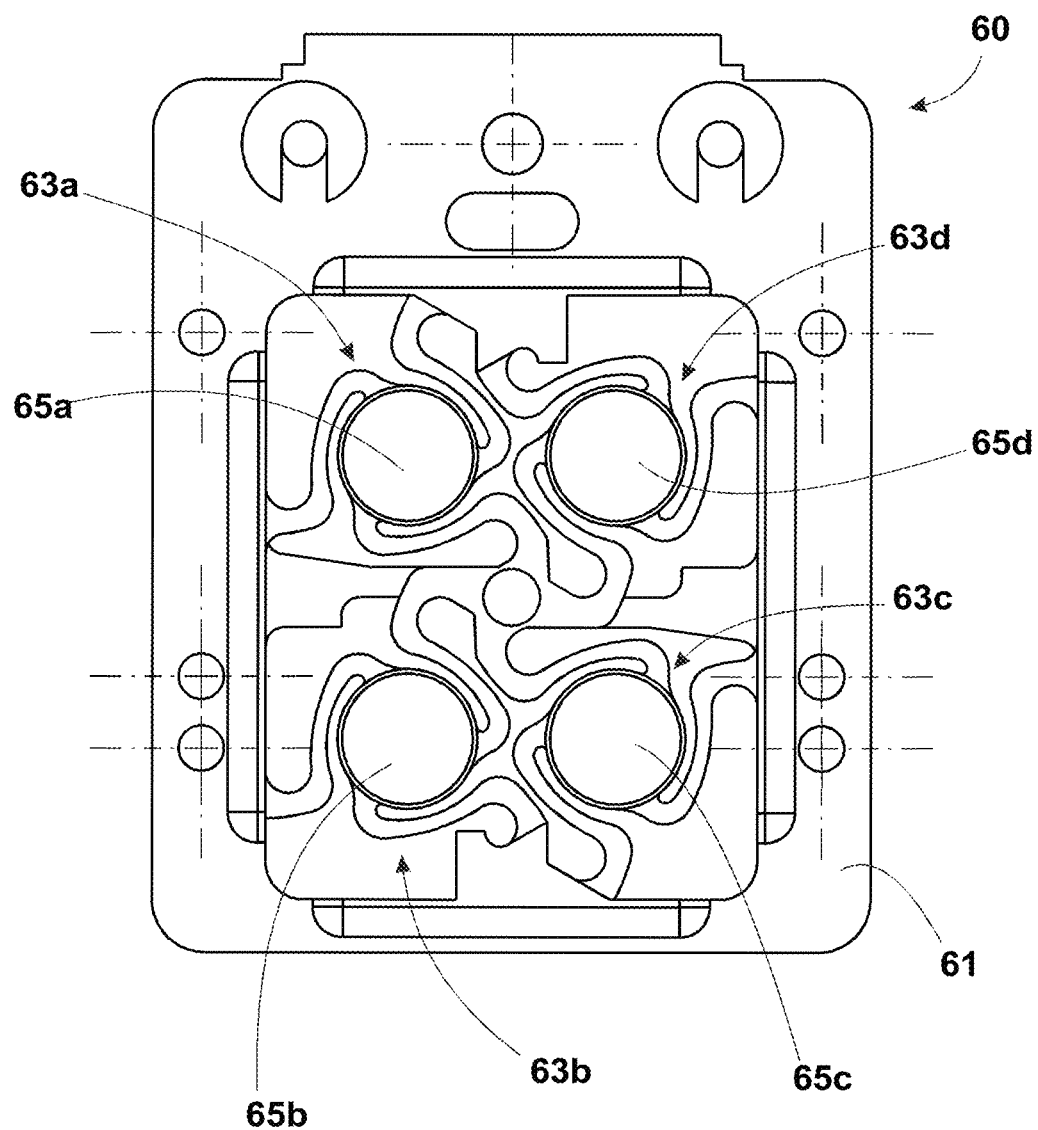
FIGS. 9 and 10 show in a plan view and in a perspective view, respectively, an alternative embodiment according to the invention, of the touching group shown in the FIGS. 7 and 8.
Figure 12:
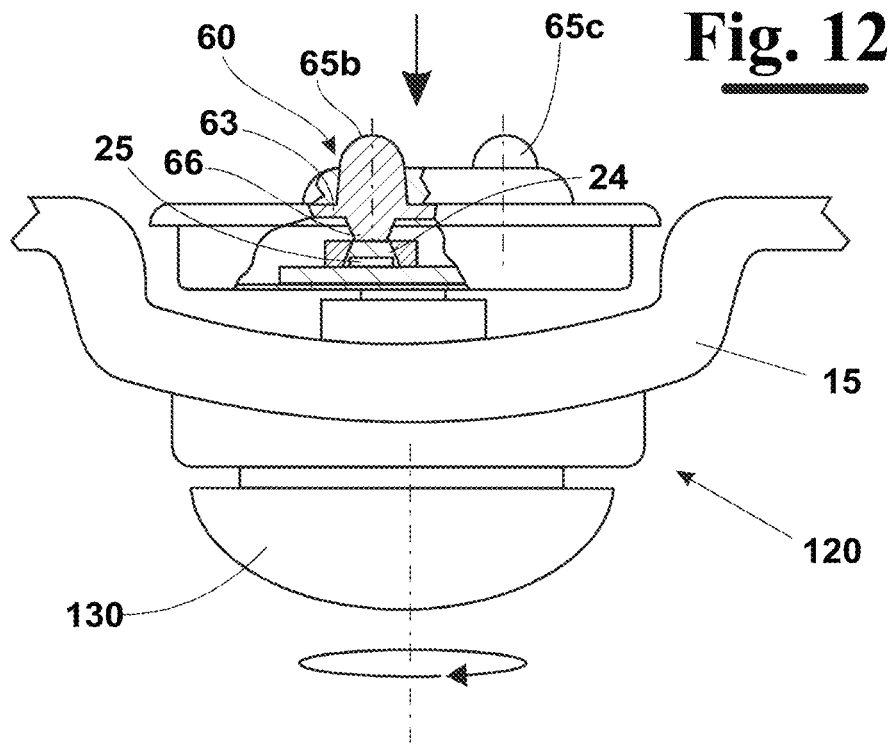
Figure 13:
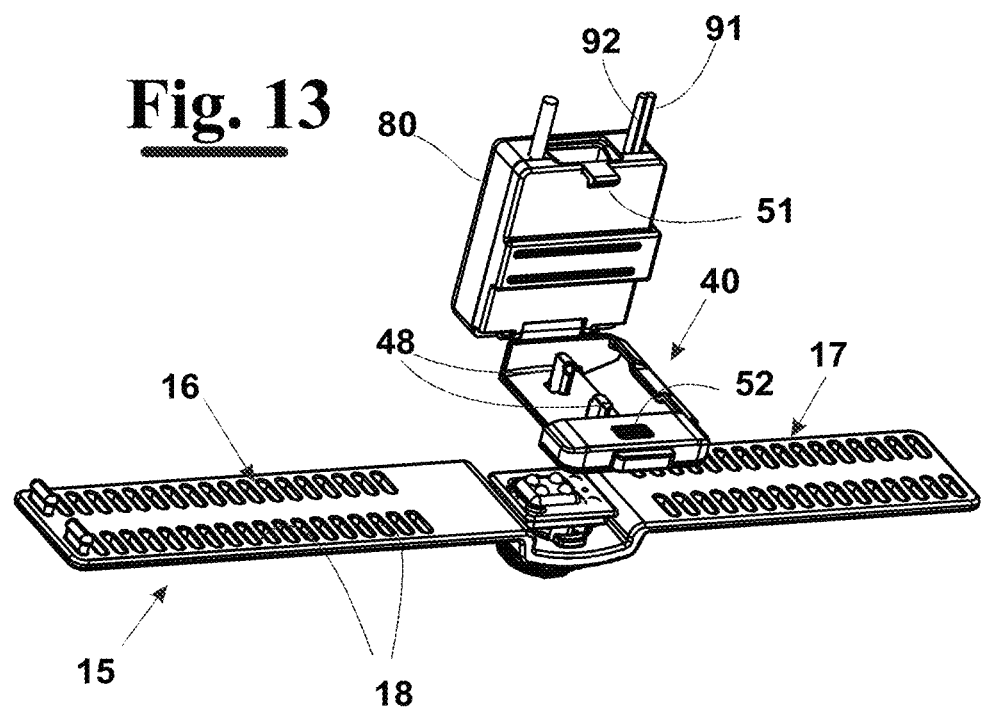
FIGS. 13 to 17 diagrammatically show an alternative embodiment of the tonometer shown in the FIG. 1 and from 3 to 6.
Figure 14:
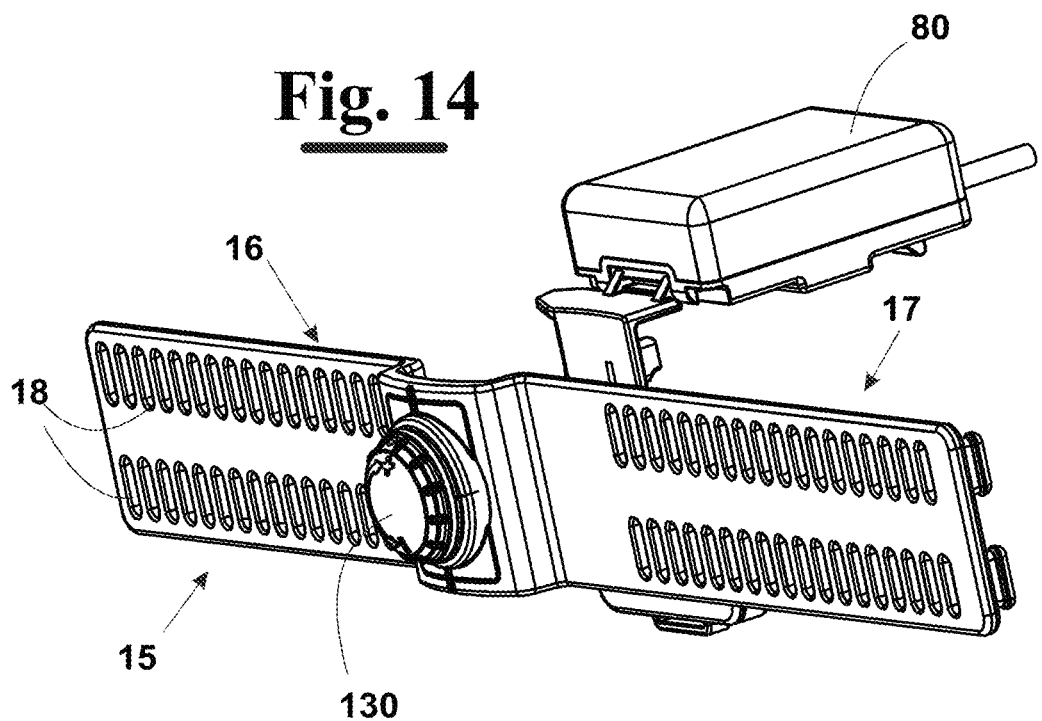

As, for example, shown in the FIGS. 8, 9 and 12, the protuberant members 65a-65d are substantially truncated cone-shaped. In particular, the transverse section of the protuberant members 65a-65d decreases going from the base portion 61 towards the wrist, and in particular towards the radial artery, of the patient 100.

In the embodiment that is shown in the FIGS. 7 and 8, the touching group 60 comprises 4 protuberant members 65a-65d positioned in a row. Therefore, in this case the detection group 20, that is not shown in the figure, have 4 pressure sensors 25 positioned in a row, each of which associated to a respective protuberant member 65a-65d.

Figure 10:
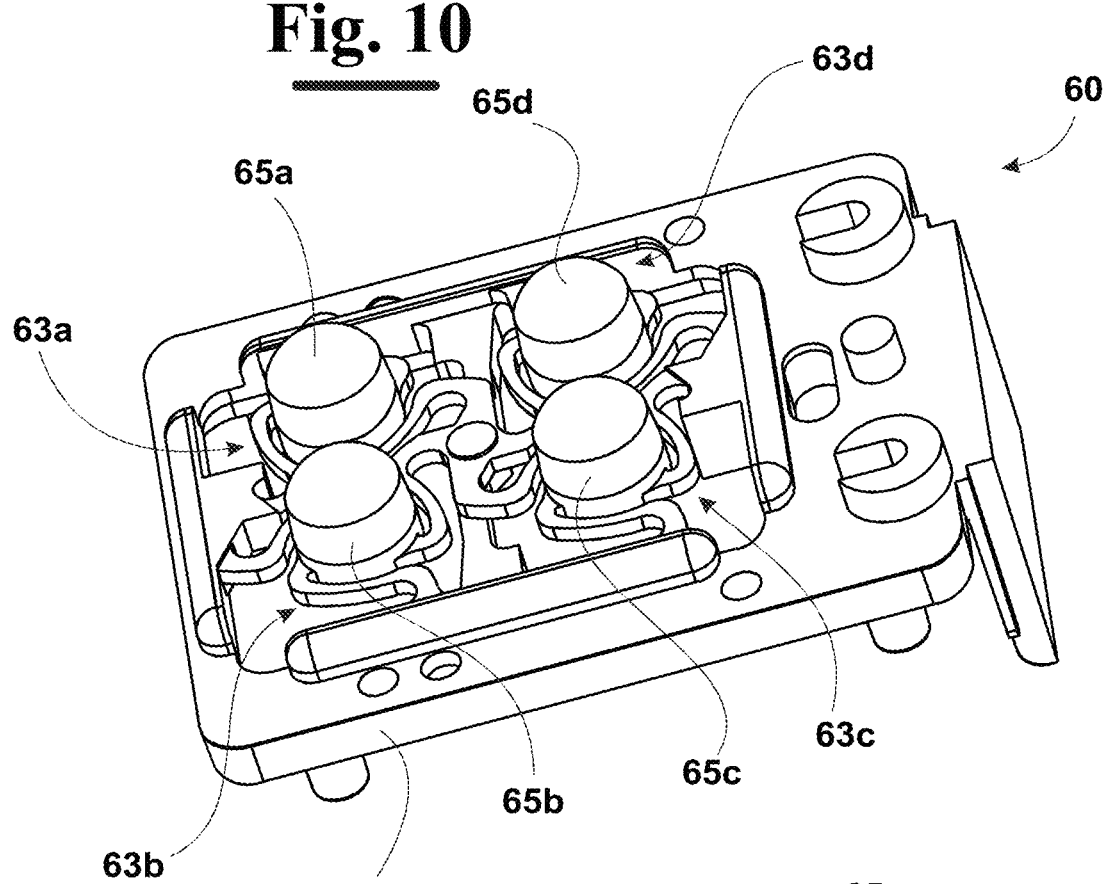

In the alternative embodiment shown in the FIGS. 9 and 10, instead, the touching group 60, still comprises 4 protuberant members 65a-65d, but this time they are positioned according to an array, which provides 2 rows and 2 columns. Therefore, in this case the detection group 20, that is not shown in the figure, have 4 pressure sensors 25 positioned according to the same array 2×2, and in which each sensor 25 is positioned at a respective protuberant member 65a-65d at the opposite side of the wrist of the patient 100.

The tonometer 1, according to the invention, can provide an adjusting device 120 arranged to bring the touching group 60 and the detection group 20, integral to it, near to the radial artery, or to move them away from it. In this way, it is possible to adjust the force F exerted by the touching group 60 on the wall of the radial artery. In fact, as well known, the detection of the signal of the arterial blood pressure can be carried out by means of a sensor of pressure, only after that a slight flattening of the artery 101 has been provided. There is, in particular, a minimum threshold value of the flattening of the artery 101 below which it is not possible to detect the blood pressure wave, and a maximum threshold value above which the occlusion of the artery 101 is caused.

The adjusting device 120 for adjusting the distance of the detection group 20 from the radial artery 101, for example a worm screw, has, therefore, the function of exerting a pressure on the wrist of the patient 100 that is high enough to produce a flattening of the artery 101 and, therefore, to allow the pressure signal to be detected by the detection group 20, but it is not too high in order to avoid the occlusion of the artery 101.

Figure 11:
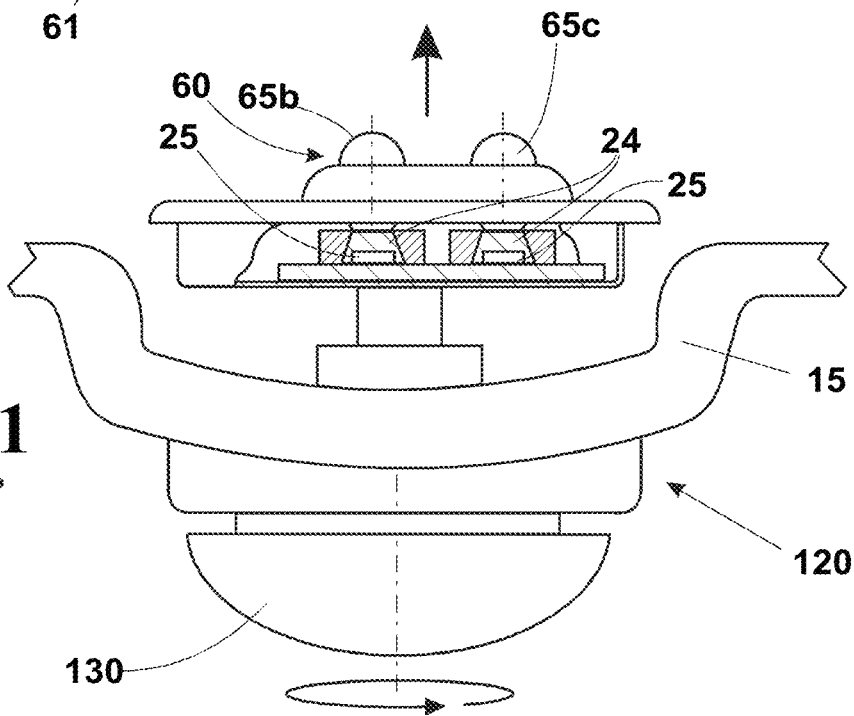
FIGS. 11 and 12 diagrammatically show, in a partially sectioned view, some components of the tonometer, according to the invention, in order to highlight some features.

More precisely, as diagrammatically shown in the FIGS. 11 and 12, the adjustment of the distance d of the detection group 20 from the artery 101 is carried out by acting on the adjusting device 120, in particular on an operating knob 130 of which it is provided, during a starting step of calibration. More precisely, if the knob 130 is rotated in a sense of rotation, for example in a clockwise sense, the sensors 25 are brought near the artery of the patient (FIG. 11). Instead, if the knob 130 is rotated in the opposite sense, for example in a counter-clockwise sense, the sensors 25 are moved away from the artery (FIG. 12).

The starting positioning of the sensors 25 with respect to the artery of the patient is generally carried out during a starting calibration step, during which a worker adjusts the distance of the detection group 20 from the radial artery 101 as above disclosed, visualizing, at the same time, the blood pressure wave on a monitor and blocking the detection group 20 in the position corresponding to a predetermined shape of the curve displayed on the monitor.

As diagrammatically shown in FIG. 4, in a particular embodiment of the invention, the bracelet 10 comprises a support portion 12 and a strap 15. This is made of a flexible material and comprises a first portion 16 and a second portion 17. In particular, the portions 16 and 17 have a respective first end 16a, 17a fixed to the support portion 12 at opposite sides, and a respective second end 16b, 17b, which is free.

Figure 5:
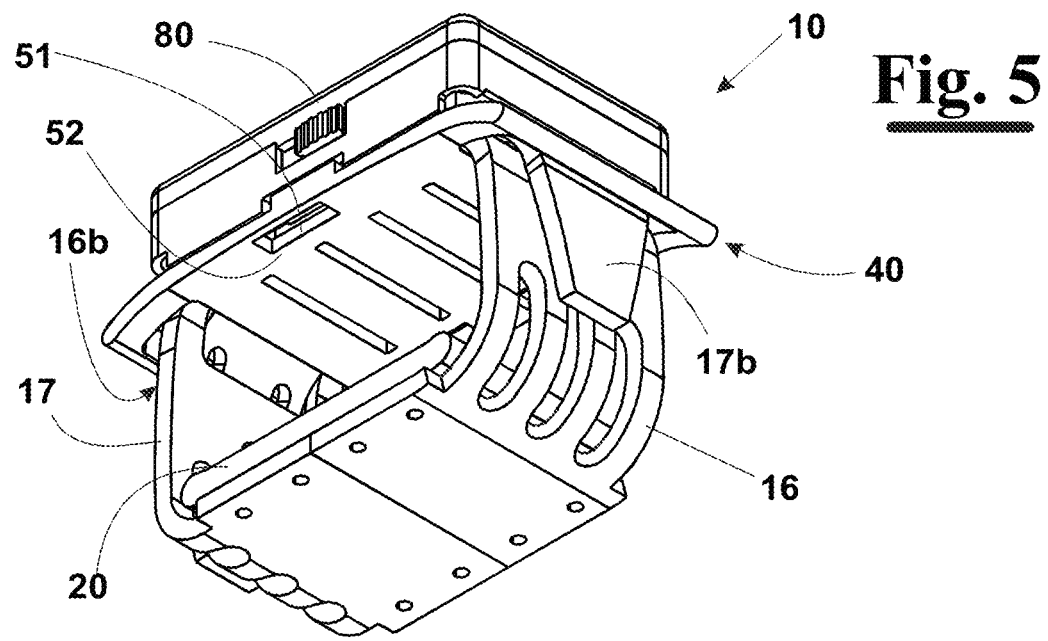
FIGS. 5 and 6 show in 2 different perspective views the strap of FIG. 3 provided with the engagement device according to the invention.
Figure 6:
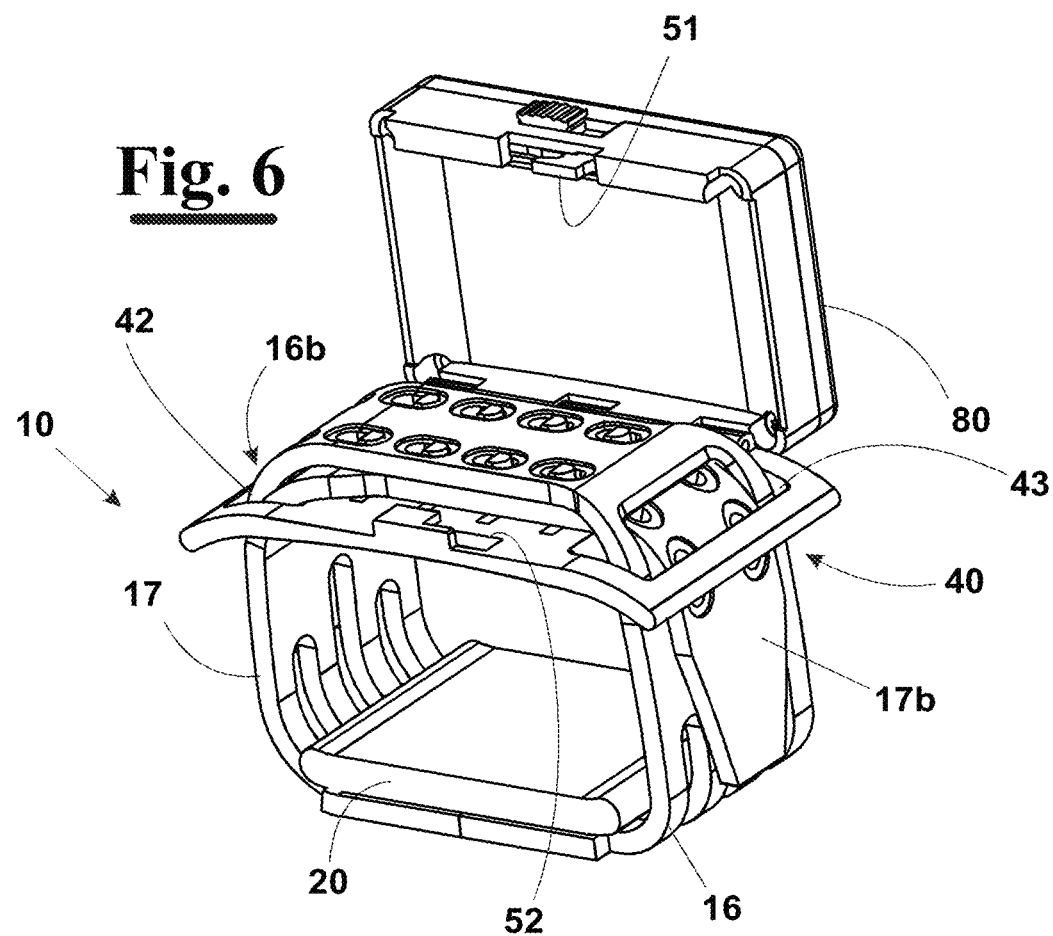

An engagement device 40 is, furthermore, provided (FIGS. 5, 6 and 13 to 17) arranged to engage, in use, the first and the second portion 16 and 17 of the strap 15. More precisely, in the embodiment shown in the FIGS. 1 and 3 to 6, the portions 16 and 17 of the strap 15 are fixed to the support portion 12 at opposite sides in such a way to be out of alignment. Therefore, in this case, the engagement device 40 is arranged to engage the portions 16 and 17 in a position in which they are arranged side by side (FIGS. 5 and 6). In the alternative embodiment of the invention shown in the FIGS. 13 to 16, instead, the 2 portions 16 and 17 are fixed at opposite sides to the support portion 12, but differently from the previous case, they are arranged aligned. Therefore, in this case, the engagement device 40 is arranged to engage the portions 16 and 17 in a position in which they are overlapped one another.

The engagement device 40 and the portions 16 and 17 of the strap 15 provide mutual engagement members. For example, in the case shown in the FIGS. 5 and 6, and in the FIGS. 13 to 17, the engagement device 40 can provide one, or more teeth, for example 2 teeth 48, arranged to engage respective holes 18, in particular elongated holes, which are made in the portions 16 and 17.

A locking device, then, contributes to provide a firm anchorage of the bracelet 10 to the arm of the patient 100, the locking device comprising, for example, a tooth 51 that is integral to the containing body 80 arranged to engage in a removable way in a respective aperture 52 provided in the engagement device 40.

Figure 17:
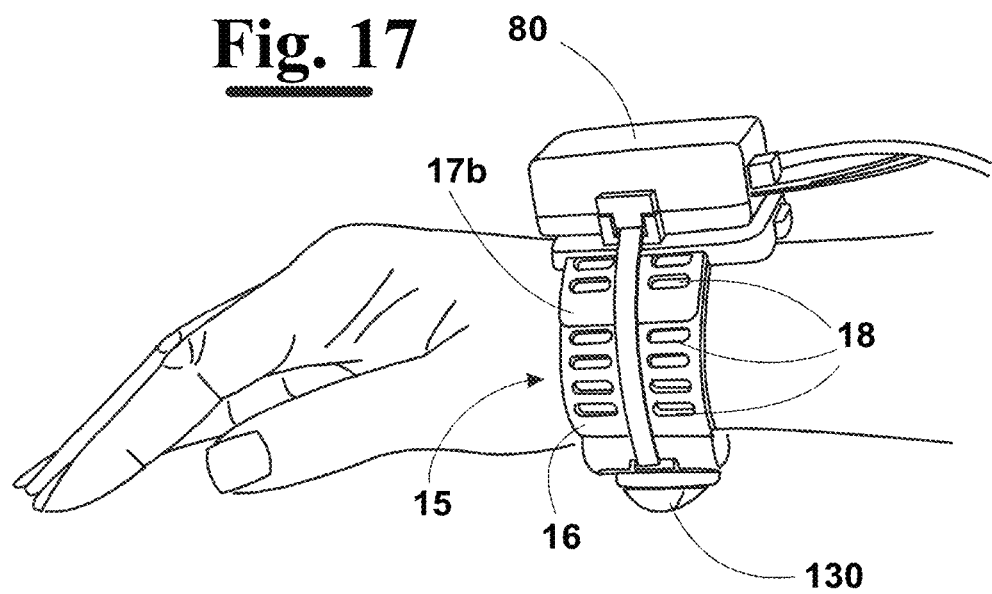

More in detail, the locking device 51, 52 is arranged to maintain the engagement device 40 and the containing body 80 in a mutual locking configuration (FIGS. 5 and 17). In this configuration, the first and the second portion 16, 17 of the strap 15, in particular at the respective free ends 16b, 17b, are tightened between the engagement device 40 and the containing body 80, in such a way to lock the bracelet 10 in a correct position with respect to the arm of the patient. In this correct position, the detection group 20 is arranged at the artery of the patient and the containing body 80 is positioned at the upper, substantially flat, part of wrist of the patient.

In the embodiment shown in the FIGS. 5 and 6, the engagement device 40 provides a main body 41. This can provide a first aperture 42 and a second aperture 43 positioned at opposite sides, and passed through, in use, respectively, by the second end of the first portion 16 and the second end of the second portion 17 of strap 15.

In both the embodiments above described, the combined use of the engagement device 40 and of the locking device 51, 52, as provided by the present invention, allows to avoid accidental movements of the bracelet 10 and, therefore, of tonometer 1 with respect to the correct position identified during the above described calibration step. Therefore, the tonometer 1, according to the invention, can be used also at home environment assuring, anyhow, a high level of accuracy in the measuring of the blood pressure wave of the patient. More precisely, the engagement device 40 allows to adjust both the length of portion 17, and the length of portion 16. Therefore, the relative position can be adjusted between the containing body 80 and the detection group 20 can be adjusted and, in particular, contributing in a determinant way to arrange the bracelet 10 in the correct position with respect to the arm of the patient. As above described, with correct position is intended the position in which the detection group 20 is positioned at the artery of the patient 100, and, at the same time, the containing body 80 is positioned at the upper, substantially flat, part of the wrist of the patient, that means in a position in which it is firm, and, at the same time, comfortable.

Figure 15:
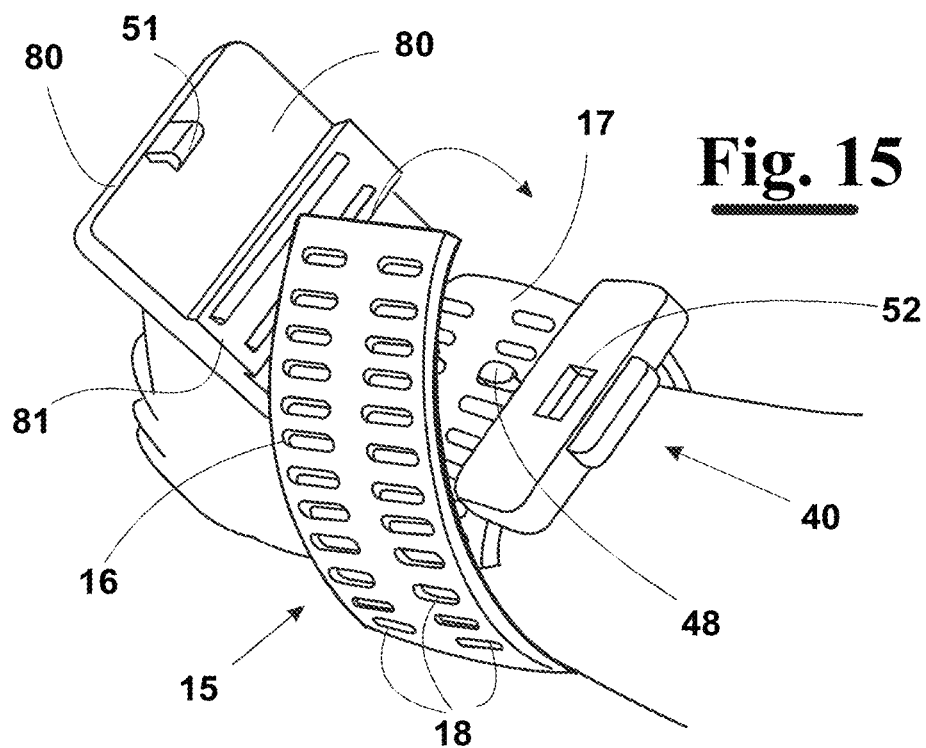
Figure 16:
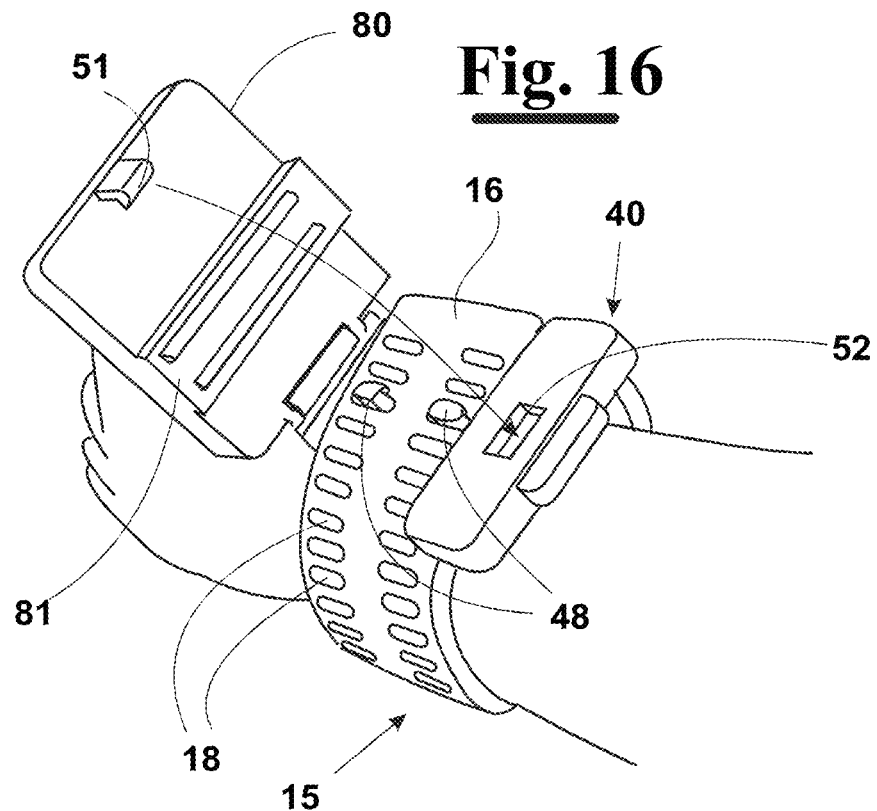

Furthermore, the containing body 80 and the engagement device 40, in particular its main body 41, can be hinged each other such that, as can be easily deduced, for example by examining the FIGS. 5 and 6, or the FIGS. 15-17, the containing body 80 can rotate about the axis 149 of the hinge 49 (see FIG. 3) with respect to the engagement device 40 in order to move from a distant position (FIGS. 6 and 16) to the locking configuration (FIGS. 5 and 17), in which the two components 40 and 80 are overlapped one another and tighten between them, as above described, the two portions 16 and 17 of the strap 15.

As diagrammatically shown in FIG. 11, the detection group 20 can provide a plurality of housings 24, each of which arranged to house a respective sensor 25. Each housing can be made of a material having a predominantly non-viscoelastic behaviour, advantageously flexible. This is arranged to transmit the external forces to the sensor contained in the housing 24.

Alternatively, each housing can be made of a stiff material inside of which a fluid material, in particular non-viscoelastic, is introduced, this on its turn polymerized, transmits the external forces to sensor 25 embedded in it. The sensitive member 25 comprises, in general, a membrane deforms according to the pressure change transmitted by the radial artery 101, with which the respective protuberant member 65a-65d is into contact.

As diagrammatically shown in FIG. 12, each protuberant member 65a-65d, therefore, transmits the detected pressure pulses to a corresponding sensor 25 through a layer of a predetermined material having a behaviour prevalently non-viscoelastic 24. In particular, at the side opposite to the one arranged in into contact with the skin of the patient undergoing examination, the protuberant member 65a-65d provides transmission portion 66. Preferably, still with reference to FIG. 12, the transmission portion 66 is substantially truncated cone-shaped. In a possible embodiment of the invention, the protuberant members 65a-65d and the connection portions 63a-63d are produced in a single piece.

As diagrammatically shown in FIG. 18, a system 500 for determining the arterial blood pressure of a patient comprises a tonometer 1 as above described with reference to FIGS. 1 to 17 arranged to generate a tonometric curve 220, and a ECG device 90 comprising 2 electrodes 91 and 92, and arranged to generate an electrocardiographic curve 220. The system 500 provides, furthermore, a microcontroller 300 arranged to process the electrocardiographic curve 210 and the tonometric curve 220 of the patient undergoing examination at determined instants (ti), each of which corresponding to cardiac pulse of the patient, for determining the pulse transit time, o PTT, i.e. the delay between le due curve. More in detail, by using known algorithms, by the tonometric curve 220 and by the pulse transit time PTT, the microcontroller 300 is arranged to measure a respective value PA2(ti) and PA1(ti) of the arterial blood pressure.

Figure 18:
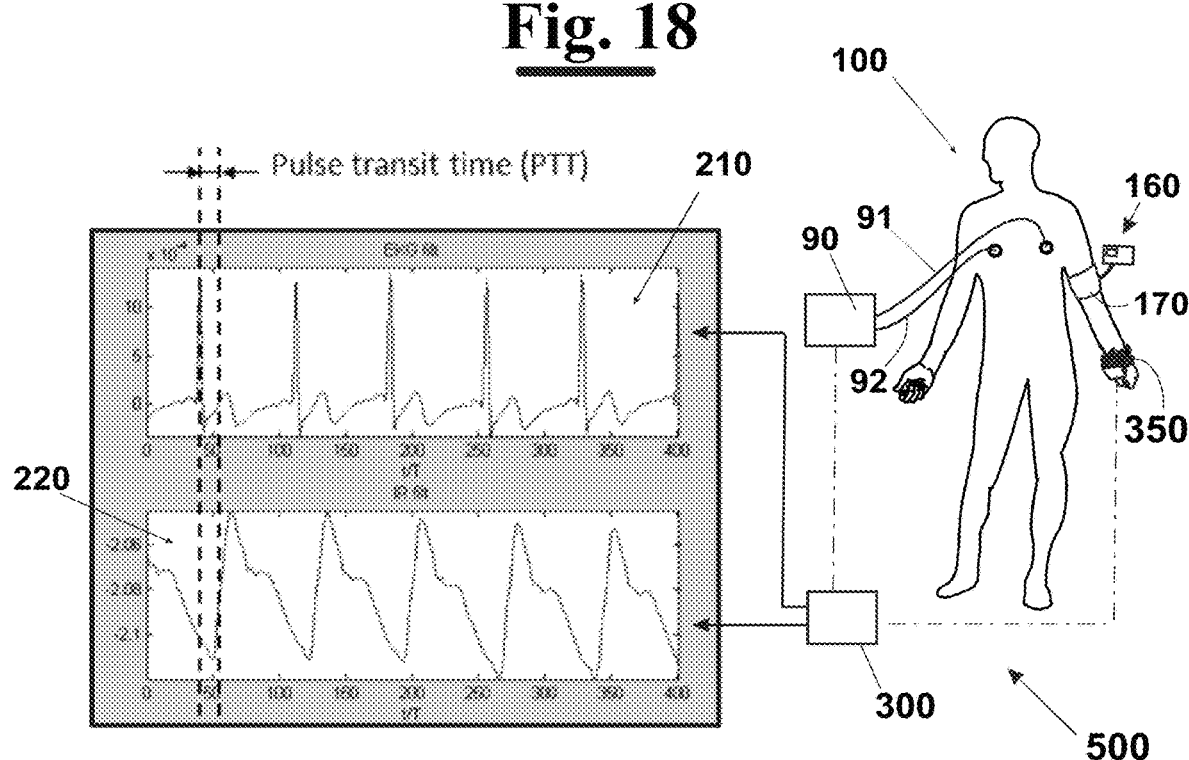
FIGS. 18 and 19 diagrammatically show the system, according to the invention, for determining the blood pressure wave of a patient.
Figure 19:
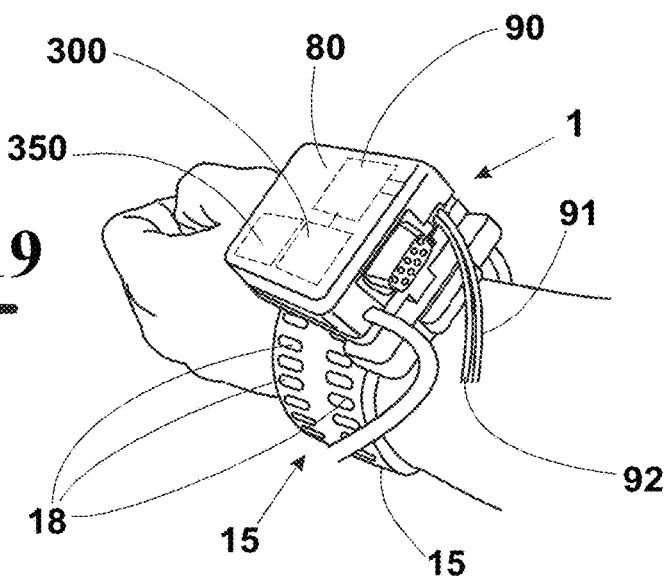

As diagrammatically shown in the FIGS. 18 and 19 the microcontroller 300, the processing unit 350 processing the data of the tonometer 1, and the ECG device 90 can be provided as 3 independent components, which are operatively connected by an appropriate wiring, or in wireless communication each other, or at least 2, or all of them, can be housed within the containing body 80 (FIG. 19).

According to the invention, the microcontroller 300 can also be arranged to measure the difference ΔPA(ti) between the value PA1(ti) of the arterial blood pressure of the patient estimated by the pulse transit time and the value PA2(ti) of the arterial blood pressure estimated by tonometric curve.

The system 500 can comprise, furthermore, an oscillometric measurement device 160 operatively connected to the microcontroller 300. As known, the oscillometric device 160 is arranged to measure the arterial blood pressure of the patient 100 by processing the air oscillations inside a muff 170 applied to the arm of the patient, during the deflating step. When the microcontroller 300 detects a difference ΔPA1(ti) between the value PA1(ti) of the arterial blood pressure measured by the pulse transit time technique, and the value PA2(ti) of the arterial blood pressure measured by the tonometer, greater than a predetermined threshold value, it operates the oscillometric device 160 obtaining in response a value of the arterial blood pressure PA3(ti) that is used by the microcontroller 300 as calibration value PAC(ti). More precisely, the microcontroller 300 associates the value PA3(ti) of the arterial blood pressure both to the arterial blood pressure value PA2(ti) determined by the tonometer 1, and to the value PA1(ti) of the arterial blood pressure determined by the pulse transit time.

The above described calibration procedure is carried out because, as known, the measurement of the arterial blood pressure value estimated by the tonometric technique, and the measurement of the arterial blood pressure value estimated by the PPT technique, are subjected to different errors. More precisely, the values PA2(ti) of the arterial blood pressure determined by the tonometer 1 are subjected to artifacts of movement, i.e. due to the movement of the bracelet 10 of the tonometer 1 with respect to the artery of the patient 100. This type of condition, as well as the flattening of the tonometric curve, or the relaxation of the strap of the bracelet 10, that affect the measurement of the arterial blood pressure through the tonometer 1 and, therefore, cause errors of measurement, do not affect the measurement of the arterial blood pressure carried out by the PTT technique, because they do not significantly modify the above described delay. On the other hand, the measurement of the values PA1(ti) estimated by the PTT technique, is affected by an artery relaxation that is caused, for example, by administering drugs, in particular a vasodilator, or adrenaline, that can cause a large error in the measurement. This event has no effect on the measurement of the values of the arterial blood pressure through tonometer 1.

In the light of the above, the tonometric technique and the PTT technique are subjected to different errors and, therefore, their combined use, as provided by the invention, allows to avoid the measurement errors due to events, or of the other type.

In fact, if any of the events above described happens, an inconsistency would be registered between the values PA1(ti) and PA2(ti), because it would affect only one of the arterial blood pressure values estimated by the 2 techniques. This inconsistency is, however, promptly corrected starting the above described calibration procedure that avoid, therefore, to incorrectly measure the values of the arterial blood pressure.

The foregoing description exemplary embodiments of the invention will so fully reveal the invention according to the conceptual point of view, so that others, by applying current knowledge, will be able to modify and/or adapt for various applications such embodiment without further research and without parting from the invention, and, accordingly, it is therefore to be understood that such adaptations and modifications will have to be considered as equivalent to the specific embodiments. The means and the materials to realize the different functions described herein could have a different nature without, for this reason, departing from the field of the invention. It is to be understood that the phraseology or terminology that is employed herein is for the purpose of description and not of limitation.

The invention claimed is:

1. A tonometer for continuously monitoring the arterial blood pressure of a patient for a predetermined period of time, said tonometer comprising:
   a bracelet configured to be applied to a wrist of a patient;
   a detection group mounted on said bracelet, and configured to detect a pressure signal, said detection group comprising a plurality of pressure sensors arranged to detect a respective pressure signal associated with the blood pressure wave of the patient, at least a pressure sensor of said plurality being configured to be positioned in proximity of a radial artery of the patient, at an opposite side of a radial bone;
   a touching group configured to be interposed between said detection group and said radial artery of said patient, said touching group comprising a plurality of protuberant members, each protuberant member of said plurality of protuberant members being configured to be positioned into contact with skin of said patient to exert a predetermined force F on said radial artery, and to transmit the received pressure pulses to a respective pressure sensor associated with said radial artery;
   a processing unit arranged to process said pressure signal detected by said detection group to determine the blood pressure wave of the patient;
   wherein said touching group is made of a predetermined material having an elastic constant greater than elastic constant of the radial artery, in that said touching group comprises a base portion that is integral to said detection group and a plurality of connection portions, each of which is arranged to elastically connect a respective protuberant member to said base portion, and in that each said connection portion of said plurality comprises a plurality of connection arms configured to have a controlled elastic flexibility along a predetermined direction orthogonal to said base portion such that each protuberant member of said plurality is elastically movable along said direction orthogonal to said base portion; and
   wherein said connection arms are S-shaped, each of said connection arms being configured to lay in a rest position on a plane orthogonal to said movement direction of said protuberant members.

2. The tonometer according to claim 1, wherein said connection arms are symmetrically arranged about said movement direction of the respective protuberant member.

3. The tonometer according to claim 1, wherein at least three connection arms are provided.

4. The tonometer according to claim 1, wherein said base portion and said protuberant members are made of a plastic material having an elastic constant greater than the elastic constant of the radial artery, and wherein said connection portions are made of a material selected from the group consisting of:
   a metallic material; and
   a plastic material.

5. The tonometer according to claim 1, wherein, between each of said protuberant members and the respective sensor, a layer is provided of a predetermined non-viscoelastic material.

6. The tonometer according to claim 1, further comprising an adjusting device configured to bring/move away said touching group near to/from said radial artery of said patient up to position said touching group in a position where the force F exerted by said touching group on the wall of said radial artery causes a predetermined flattening of said radial artery.

7. The tonometer according to claim 6, wherein said adjusting device comprises a worm screw, on which said touching group is slidingly mounted, and wherein an adjusting handle is provided acting on which a sliding of said touching group is operated along said worm screw.

8. The tonometer according to claim 1, wherein each protuberant member of said plurality is truncated cone-shaped where the transverse section decreases going from said base portion towards said radial artery of said patient.

9. The tonometer according to claim 1, wherein said detection group comprises at least three pressure sensors positioned in a row, and said touching group comprises at least three respective protuberant members positioned in a row.

10. The tonometer according to claim 1, wherein said bracelet comprises:
a containing body arranged to house said processing unit;
a support portion arranged to engage said detection group;
a strap made of a flexible material, and comprising a first portion and a second portion having a respective first end that is fixed to said support portion at opposite sides, and a respective second end, which is free;
an engagement device arranged to engage said first and said second portion of said strap;
a locking device arranged to maintain, in a locking configuration, said engagement device and said containing body in said locking configuration, said first and said second portion of said strap being tightened between said engagement device and said containing body to maintain said bracelet in a correct position with respect to the arm of the patient, in which said detection group is configured to be positioned at the radial artery of the patient, and said containing body is configured to be positioned at the upper part of the wrist of the patient that is flat.

11. The tonometer according to claim 10, wherein said first and said second portion of said strap are fixed to said support portion at opposite sides, said first and said second portion of said strap configured to be positioned side by side when fixed to said engagement device.

12. The tonometer according to claim 10, wherein said first and said second portion of said strap are fixed to said support portion at opposite sides, said first and said second portion of said strap configured to overlap with one another when fixed to said engagement device.

13. The tonometer according to claim 10, wherein said engagement device provides at least one tooth arranged to engage in a respective hole made in said portions of said strap, and wherein the locking device is, furthermore, provided arranged to maintain said containing body and said engagement device in a mutual locking configuration.

14. The tonometer according to claim 11, wherein said engagement device provides a main body having a first aperture and a second aperture positioned at opposite sides, and passed through by said second free end of said first portion, and by said second free end of said second portion, respectively.

15. The tonometer according to claim 10, wherein said containing body and said engagement device are connected by means of a hinge having a rotation axis, said containing body configured for rotating about said rotation axis with respect to said engagement device to move from a distant position to a locking configuration, or vice versa.

16. A system for determining the arterial blood pressure of a patient, comprising:
a) a tonometer arranged to generate a tonometric curve and comprising:
a bracelet configured to be applied to a wrist of a patient;
a detection group mounted on said bracelet and configured to detect a pressure signal, said detection group comprising a plurality of pressure sensors arranged to detect a respective pressure signal associated with the blood pressure wave of the patient, at least a pressure sensor of said plurality being configured to be positioned in proximity of a radial artery of the patient, at an opposite side of a radial bone;
a touching group configured to be interposed between said detection group and said radial artery of said patient, said touching group comprising a plurality of protuberant members, each protuberant member of said plurality of protuberant members being configured to be positioned into contact with skin of said patient to exert a predetermined force F on said radial artery, and to transmit the received pressure pulses to a respective pressure sensor associated with said radial artery;
a processing unit arranged to process said pressure signal detected by said detection group to determine the blood pressure wave of the patient;
wherein said touching group comprises a predetermined material having an elastic constant greater than elastic constant of the radial artery, in that said touching group comprises a base portion that is integral to said detection group and a plurality of connection portions, each of which is arranged to elastically connect a respective protuberant member to said base portion, and in that each said connection portion of said plurality comprises a plurality of connection arms configured to have a controlled elastic flexibility along a predetermined direction orthogonal to said base portion, such that each protuberant member of said plurality is suitable to elastically move along said direction orthogonal to said base portion; and
wherein said connection arms are S-shaped, each of said connection arms being configured to lay in a rest position on a plane orthogonal to said movement direction of said protuberant members;
b) an ECG device arranged to generate an electrocardiographic curve;
c) an oscillometric device arranged to measure an arterial blood pressure value PA3(ti) by an oscillometric technique; and
d) a microcontroller arranged to process said electrocardiographic curve and said tonometric curve at determined instants for determining the pulse transit time, which is the delay between said electrocardiographic curve and said tonometric curve, said microcontroller being arranged to associate said computed delay to a determined reference value of the arterial blood pressure and to measure at said determined instants (ti), a difference ΔPA(ti) between a value PA1(ti) of the arterial blood pressure of the patient, that is estimated by using the pulse transit time, and a value PA2(ti) of the arterial blood pressure that is estimated by said tonometric curve, said microcontroller arranged to operate said oscillometric device, and to associate said arterial blood pressure value PA3(ti) both to the value PA2(ti) of arterial blood pressure that is estimated by the tonometric curve, and to the value PA1(ti) of arterial blood pressure that is estimated by pulse transit time.

* * * * *